United States Patent [19]
Wolzinger et al.

[11] Patent Number: 5,271,410
[45] Date of Patent: Dec. 21, 1993

[54] CATHETER WITH RAPID RESPONSE THERMISTOR AND METHOD

[75] Inventors: Renah Wolzinger, Laguna Niguel; Su S. Soong-Wu, Irvine, both of Calif.

[73] Assignee: Baxter International Inc., Deerfield, Ill.

[21] Appl. No.: 678,911

[22] Filed: Apr. 1, 1991

[51] Int. Cl.⁵ .......................... A61B 5/02; A61B 5/00; A61M 31/00; A61M 25/00
[52] U.S. Cl. ................................. 128/692; 128/736; 604/53; 604/93; 604/280
[58] Field of Search ............... 128/692, 693, 658, 736, 128/742; 604/93, 96, 280, 53, 246; 606/191, 192

[56] References Cited

U.S. PATENT DOCUMENTS

| | | |
|---|---|---|
| 3,359,974 | 12/1967 | Khalil . |
| 3,595,079 | 7/1971 | Grahn . |
| 3,618,590 | 11/1971 | Frank ................................... 128/399 |
| 3,726,269 | 4/1973 | Webster, Jr. . |
| 3,995,623 | 12/1976 | Blake et al. . |
| 4,328,806 | 5/1982 | Cooper . |
| 4,329,994 | 5/1982 | Cooper . |
| 4,467,163 | 8/1984 | Pauly et al. . |
| 4,513,749 | 4/1985 | Kino et al. . |
| 4,632,125 | 12/1986 | Webler et al. . |
| 4,651,751 | 3/1987 | Swendson et al. . |
| 4,718,423 | 1/1988 | Willis et al. .......................... 128/634 |
| 4,726,383 | 2/1988 | Cook et al. . |
| 4,750,497 | 6/1988 | Suzuki et al. . |
| 4,796,640 | 1/1989 | Webler . |
| 4,841,981 | 6/1989 | Tanabe et al. . |
| 4,858,615 | 8/1989 | Meinema . |
| 4,901,734 | 2/1990 | Griffin et al. . |

FOREIGN PATENT DOCUMENTS 0303757 2/1989 European Pat. Off. .

*Primary Examiner*—Randall L. Green
*Assistant Examiner*—A. Zuttarelli
*Attorney, Agent, or Firm*—Bruce M. Canter; Debra D. Condino; Gordon L. Peterson

[57] ABSTRACT

A catheter for measuring the temperature of a fluid in a living body comprising an elongated tube having at least one lumen extending longitudinally within the tube and an opening in a peripheral wall of the tube. A thermistor mounting body mounts a thermistor in the lumen adjacent the opening. The thermistor mounting body defines a cavity at the opening which opens radially outwardly, and the thermistor is partially within the mounting body and projects from the mounting body into the cavity. There is at least one conductor in the tube with at least a region of the conductor being in the lumen and extending along the lumen to the thermistor. The region of the conductor is electrically coupled to the thermistor. The region of the conductor extends longitudinally of the lumen from a location in the lumen proximally of the thermistor to a location at which the conductor is electrically coupled to the thermistor. The mounting body may include a matrix of electrical insulating material and a filler carried by the matrix, with the filler being more thermally conductive than the electrical insulating material. In addition, by providing a multi-lumen catheter, certain of the lumens can be used to thermally insulate the thermistor from any lumen adapted to carry fluid past the location of the thermistor in the catheter.

28 Claims, 4 Drawing Sheets

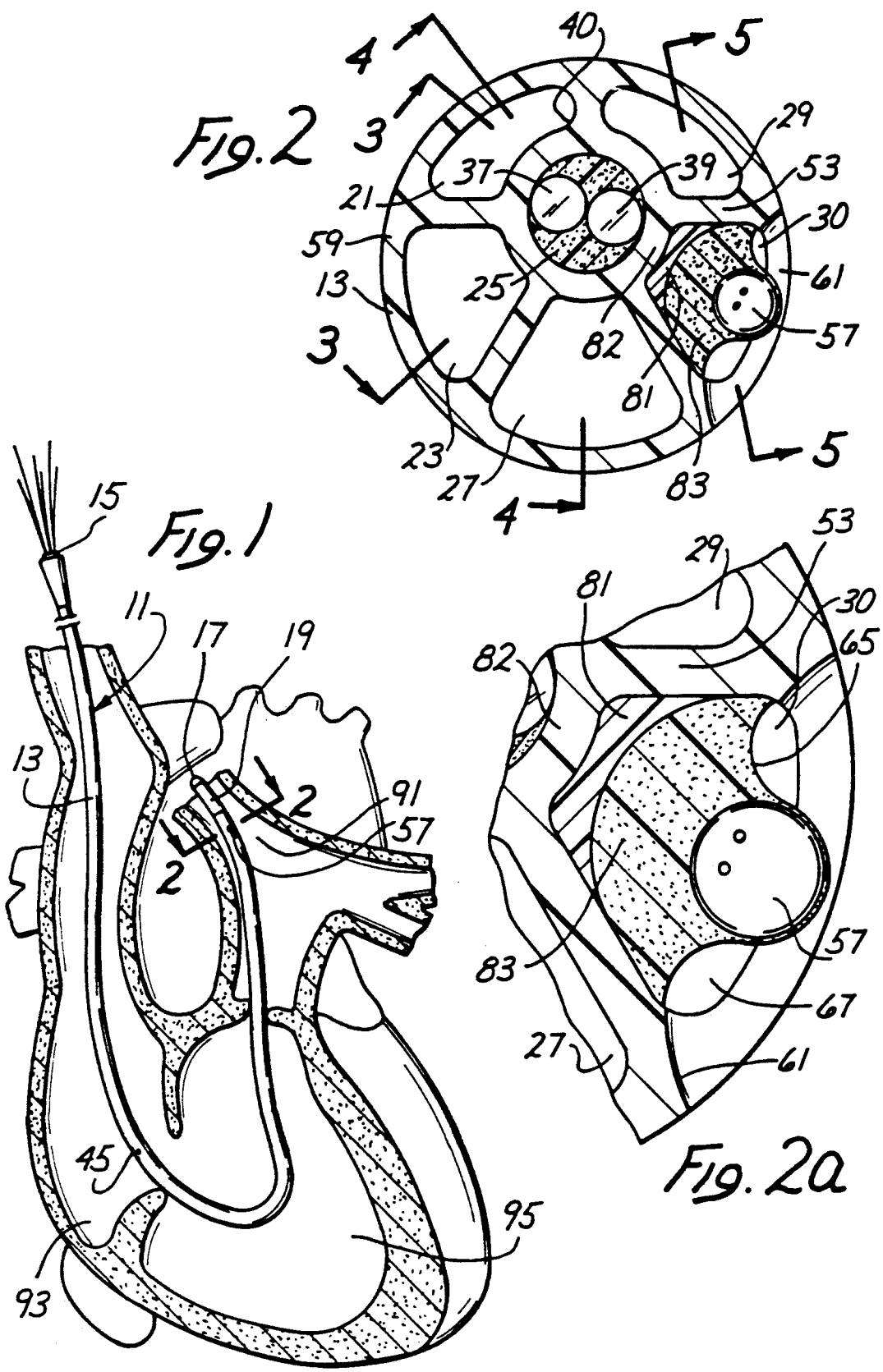

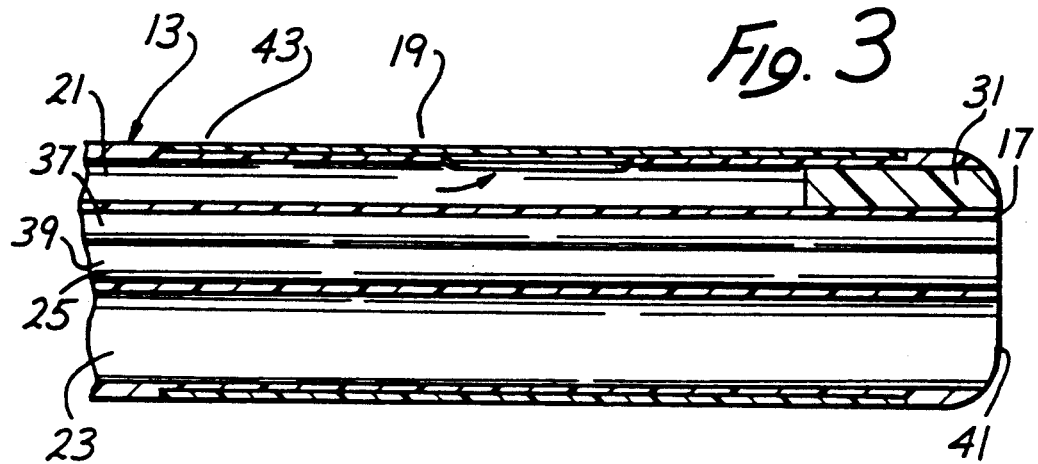
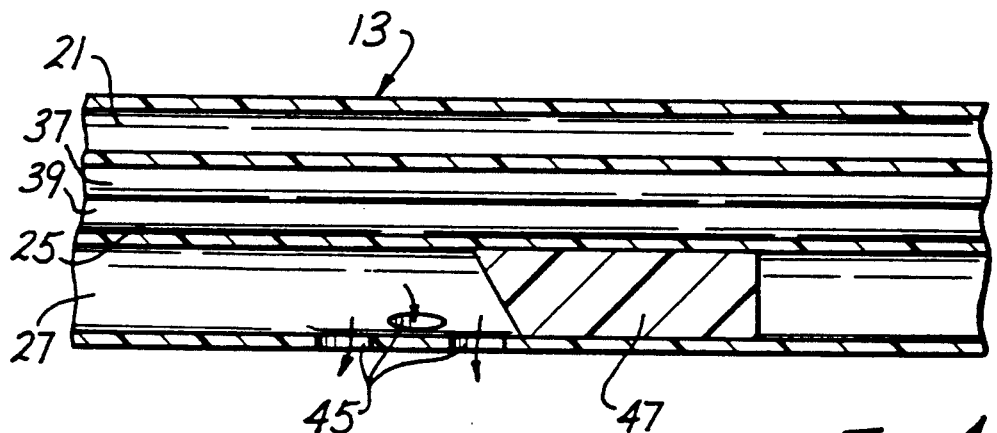
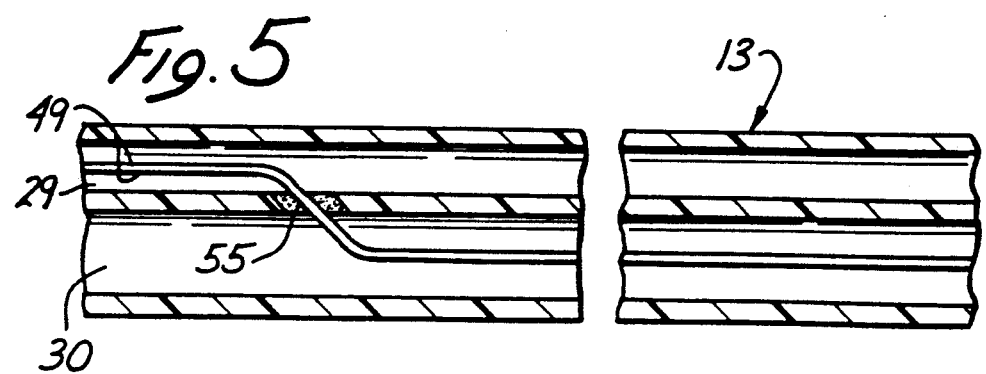

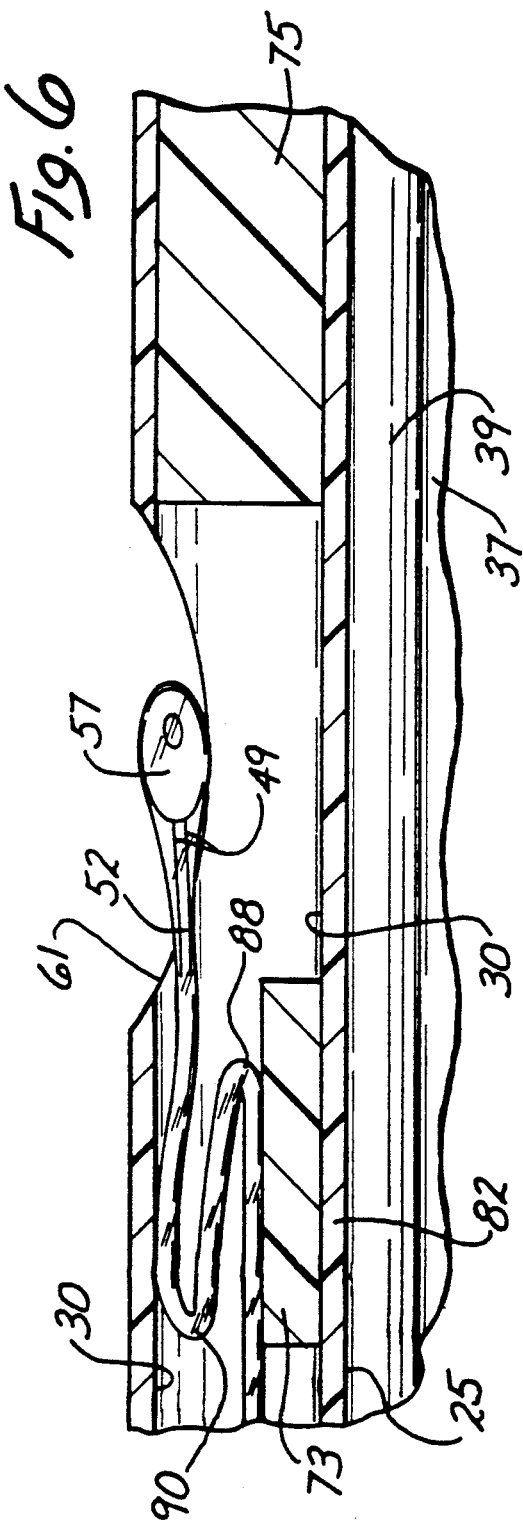
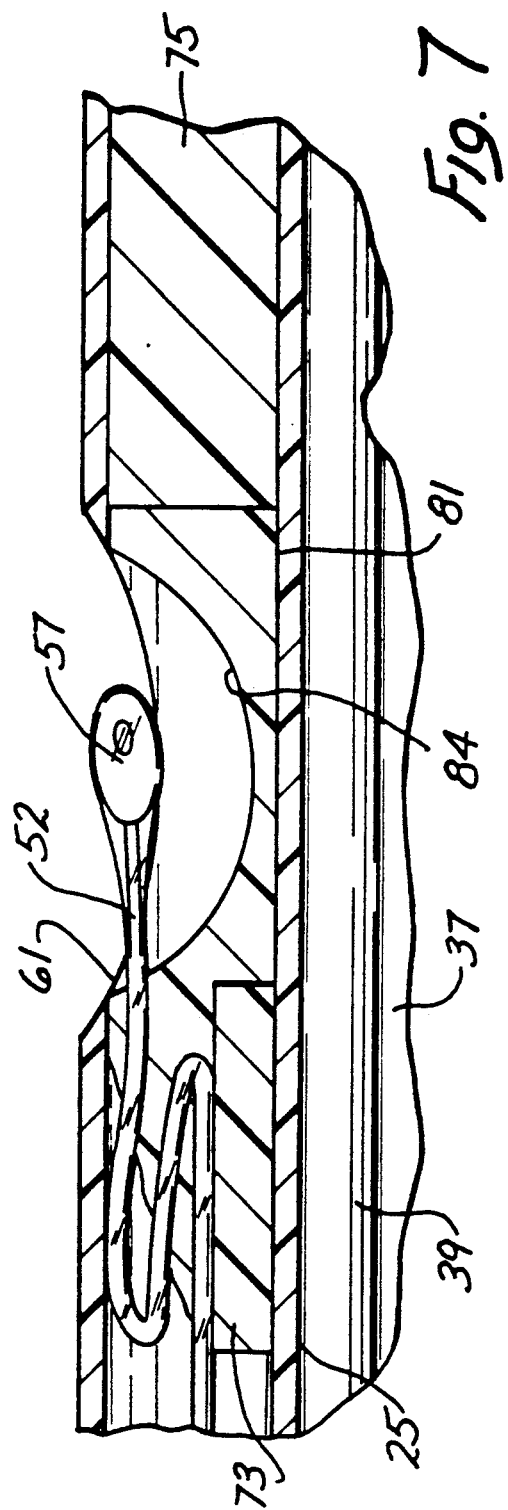

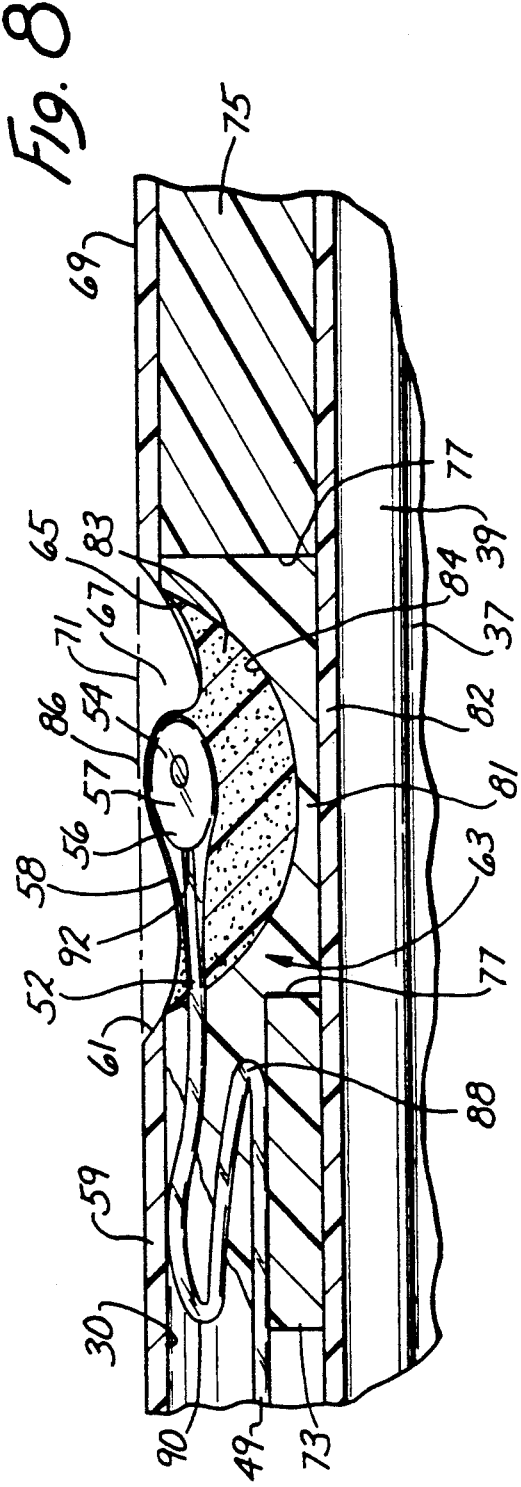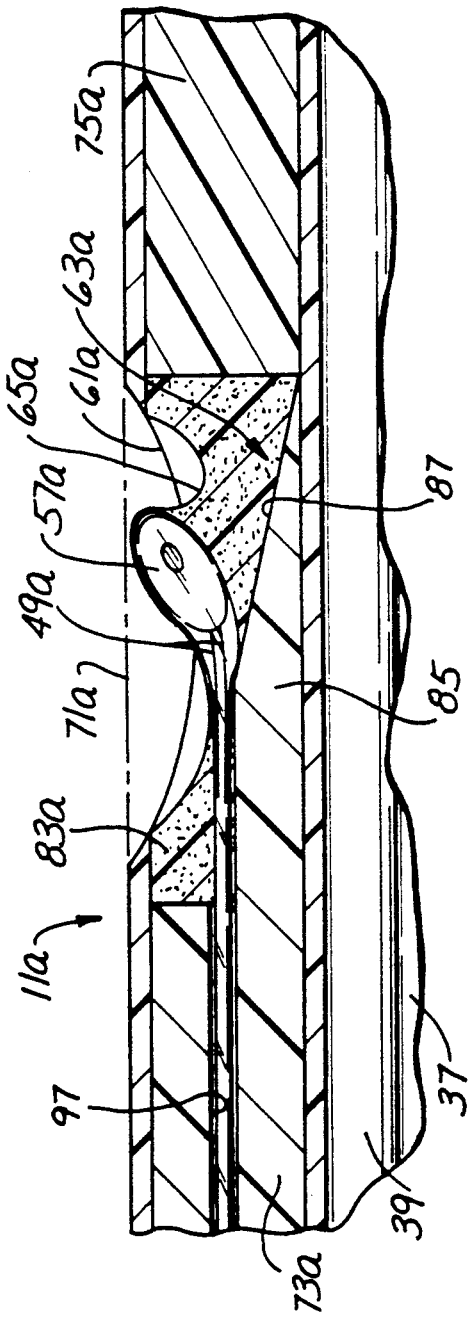

CATHETER WITH RAPID RESPONSE THERMISTOR AND METHOD

BACKGROUND OF THE INVENTION

This invention relates to catheters, and more particularly, to a catheter carrying a thermistor which has a fast response to temperature changes.

It is often necessary or desirable to measure the temperature of a fluid, such as blood, within a living body and to measure changes in temperature rapidly as they occur. One example of a medical procedure which requires a catheter having a fast response thermistor is the calculation of ejection fraction. In calculating ejection fraction, it is necessary to measure changes in blood temperature as they occur. This means that it is necessary that the thermistor measure blood temperature directly rather than the temperature of the catheter on which it is mounted. In the calculation of ejection fraction, the thermistor should follow the beat-to-beat blood temperature changes so that discrete steps in the temperature curve can be observed.

Webler U.S. Pat. No. 4,796,640 discloses a catheter with a fast response thermistor suitable for use in the calculation of ejection fraction. In the specific embodiment of this patent, the thermistor is oriented with its long axis extending radially, and the conductor leading to the thermistor is bent to provide a radially extending portion that electrically couples the conductor to the thermistor. The bent portion of the conductor controls the height of the thermistor in the catheter and the bend occurs generally in the region where external conductors are bonded to the lead wires of the thermistor.

SUMMARY OF THE INVENTION

This invention provides a catheter with a fast response thermistor which eliminates the radially extending portion of the thermistor of the Webler patent. In addition, with this invention, the thermistor is preferably oriented with its long axis extending generally longitudinally of the thermistor lumen in which it is mounted.

More specifically, the conductor leading to the thermistor extends generally longitudinally of the thermistor lumen from a location in the lumen proximally of the thermistor to the thermistor. This simplifies manufacturing and assembly in that the conductor need not be bent to provide the radial portion of the prior art, and the long axis of the thermistor may, if desired, extend generally longitudinally of the thermistor lumen. In addition, with this invention, it is not necessary to bend the conductors for the purpose of controlling the height of the thermistor, and there are no permanent bends adjacent the region where the conductors are bonded to the thermistor; however, a gentle, large radius in this region of the wires, while not preferred, is considered acceptable.

Stated differently, the region of the conductor from a location in the lumen proximally of the thermistor to the thermistor is devoid of any sharp permanent bends and is preferably unkinked. Preferably, such region between such location and the thermistor is essentially straight and is not permanently deformed.

In order that the thermistor will have a fast response characteristic as mounted on the catheter, the catheter includes an elongated tube having an opening in its peripheral wall which extends from the thermistor lumen to the exterior of the tube. A thermistor mounting body is provided in the lumen adjacent the opening. The thermistor mounting body at least partially defines a cavity at the opening with the cavity opening radially outwardly. The thermistor is at least partially within the mounting body. To provide the thermistor with fast-response characteristics as mounted on the catheter, it projects from the mounting body into the cavity. Consequently, the portion of the thermistor which projects into the cavity is in good heat-transfer relationship to the fluid within the body. In this respect, the invention differs from various prior art catheters in which a mounting body does not provide a cavity, and the thermistor does not extend into such cavity so that true fast response is not obtained.

To protect the thermistor from shearing off when, for example, the apparatus is withdrawn from a tubular introducer, the thermistor preferably does not extend radially outwardly of the cavity. Stated differently, the tube has a body line, and the thermistor extends radially outwardly no farther than about the body line.

The mounting body preferably adheres to the thermistor and the tube so it can mount the thermistor on the tube. The mounting body also serves to thermally insulate the thermistor from any adjacent lumens and provides electrical insulation for the portion of the thermistor that is within the mounting body. The mounting body can also be used to control the height of the thermistor and to assure that it does not extend radially beyond the body line.

Although the thermistor is preferably thermally insulated from the tube or catheter body in order to have a fast response, it is preferably not thermally insulated from the blood or other body fluid, the temperature of which is to be measured. To provide for electrical insulation and better thermal conductivity where that latter property is desired, the mounting body preferably includes a matrix of electrical insulating material and a filler carried by the matrix. To make the mounting body more thermally conductive, the filler is constructed of a material which is more thermally conductive than the electrical insulating material of the matrix. For example, the filler may be constructed of a ceramic, carbon or a metal. Of these materials, a ceramic is preferred because it is less electrically conductive than typical metals or carbon.

To deal with the inconsistent requirements of good thermal conductivity to the body fluid and good thermal insulation with respect to the tube or catheter body, the mounting body may also include a base of electrical insulating material between the wall of the thermistor lumen and the thermistor. With this construction, the matrix contacts the thermistor and is adjacent the base to provide better thermal conductivity where it is desired. The base thermally insulates the thermistor from the tube. For example, the electrical insulating material of the base and matrix may be a polymeric material, such as urethane or an epoxy. When the matrix and filler are used, they may also be used, if desired, to retain or assist in retaining the thermistor in the thermistor lumen.

Although the mounting body may take different forms, in one embodiment, it includes an insert received in the thermistor lumen and having a ramp for supporting the thermistor and means for retaining the thermistor on the ramp. By using the ramp, the height of the thermistor can be easily adjusted during manufacture by moving the thermistor longitudinally along the ramp.

This can be used as an aid in controlling the height of the thermistor.

In one preferred construction, the tube includes a plurality of lumens, including a central lumen and first and second separating lumens. In this embodiment, the central and separating lumens are between the thermistor lumen and a through lumen so that they can thermally insulate the thermistor from any fluid carried by the through lumen. In using the catheter of this embodiment, fluid may be introduced into the through lumen and it may be allowed to flow to the radial zone of the tube which contains the thermistor, and the central and separating lumens are used to insulate the thermistor from the fluid in this radial zone.

The invention, together with additional features and advantages thereof, may best be understood by reference to the following description taken in connection with the accompanying illustrative drawings.

BRIEF DESCRIPTION OF THE DRAWINGS

FIG. 1 is a sectional view of the human heart showing one example of how the catheter of this invention can be used.

FIG. 2 is a sectional view taken generally along line 2—2 of FIG. 1.

FIG. 2a is an enlarged, fragmentary sectional view of a portion of FIG. 2.

FIG. 3 is a fragmentary, longitudinal, sectional view through a distal region of the catheter taken on the plane of line 3—3.

FIG. 4 is a fragmentary, longitudinal, sectional view illustrating the region of the catheter adjacent the injectate port taken on the plane of line 4—4 in FIG. 2.

FIG. 5 is a fragmentary, longitudinal, sectional view illustrating the cross-over of the thermistor wires and taken on the plane of line 5—5 of FIG. 2.

FIG. 6 is a fragmentary, longitudinal sectional view illustrating the region of the catheter adjacent the thermistor prior to installation of the mounting body.

FIG. 7 is a sectional view similar to FIG. 6 after one layer of potting material has been deposited.

FIG. 8 is a sectional view similar to FIG. 6 showing the completed thermistor mounting body in place in the thermistor lumen.

FIG. 9 is a sectional view similar to FIG. 6 showing an alternate embodiment of the invention.

DESCRIPTION OF THE PREFERRED EMBODIMENT

FIG. 1 shows a catheter 11 constructed in accordance with the teachings of this invention. The catheter 11 includes an elongated, flexible catheter body or tube 13 sized to be received within a vein or artery and moved into the heart as shown, for example, in FIG. 1. The catheter 11 has a proximal end 15 and a distal end 17 and includes a balloon 19 adjacent the distal end.

The catheter 11 has a plurality of lumens, including a balloon inflation lumen 21 (FIG. 2), a through lumen 23, a central lumen 25, an injectate lumen 27, electrical wires lumen 29 and a thermistor lumen 30. All of the lumens extend longitudinally within the tube 13 from the proximal end 15 to the distal end 17. However, the balloon inflation lumen 21 is plugged by a plug 31 at the distal end 17 as shown in FIG. 3. The injectate lumen 27, the electrical wires lumen 29 and the thermistor lumen 30 are similarly plugged at the distal end 17. In addition, the central lumen 25 carries an illuminating optical fiber 37 and an imaging optical fiber 39 (FIGS. 2 and 3) and is fully closed or plugged by these fibers and an adhesive 40 which retains these fibers in the central lumen 25. The optical fibers 37 and 39 extend completely through the central lumen 25 from the proximal end 15 to the distal end 17. Accordingly, only the through lumen 23 (FIGS. 2 and 3) is capable of conducting a fluid completely through the catheter 11 from the proximal end 15 to the distal end 17. The through lumen 23 terminates in a distal port 41 (FIG. 3) at the distal end 17 of the catheter.

The balloon inflation lumen 21 extends from the proximal end 15 of the catheter 11 to the balloon 19 (FIG. 3). Although various different balloon constructions can be employed, in this embodiment, there is an annular groove 43 in a distal region of the tube 13, and the balloon 19 is received within the groove 43 and is adhered to the tube 13 in accordance with conventional practice.

The injectate lumen 27 (FIG. 4) extends from the proximal end 15 of the catheter 11 to an injectate port 45 which may comprise multiple holes in the wall of the tube. The injectate lumen 27 is plugged just distally of the injectate port 45 by a plug 47 adhered to the tube 13 within the lumen 27.

Electrical conductors 49 (FIG. 5) in the form of insulated wires extend from the proximal end 15 through the electrical wires lumen 29 to a location just distally of the injectate port 45 and then cross over into the thermistor lumen 30 in accordance with known practice. Specifically, the conductors 49 extend through an aperture in a wall 53 of the tube 13 which separates the lumens 29 and 30, and the aperture is sealed around the conductors 49 by a suitable adhesive 55.

The conductors 49 extend within the thermistor lumen 30 to a thermistor 57 (FIG. 8). The conductors 49 include a short segment coupled to the thermistor 57 and a long segment which extends through the tube 13 and which is bonded to the short segment at a bond location 52. The thermistor 57 includes the usual chip 54 and glass bead 56. In addition, the thermistor may be considered as including a thin layer 58 (FIG. 8) of electrical insulating material which covers the glass bead 56 and provides saline protection. The tube 13 has a peripheral wall 59 (FIGS. 2 and 8) and an opening 61 in the peripheral wall which extends from the thermistor lumen 30 to the exterior of the tube 13.

The thermistor 57 is mounted within the thermistor lumen 30 by a thermistor mounting body 63 as shown in FIG. 8. The mounting body 63 has a somewhat concave outer surface 65 which cooperates with the tube 13 to define a cavity 67 which opens radially outwardly at the opening 61.

The thermistor 57 is partially embedded in the mounting body 63 and projects from the mounting body into the cavity 67. The thermistor 57 projects into the cavity 67 so that fluid can enter and flow through the cavity, and the thermistor is in good heat-transfer relationship to the fluid passing over the catheter 11 at that location. A portion of the volume of the cavity 67 is occupied by the thermistor. The opening 61 and the cavity 67 are sufficiently large so that fluid flowing along the tube 13 can readily flow over the portion of the thermistor 57 which projects into the cavity 67. This places the thermistor 57 in good heat-transfer relationship to any fluid flowing along the tube 13 at that location.

The thermistor 57 is elongated and is oriented so that its longitudinal dimension extends generally longitudinally of the thermistor lumen 30. Thus, the long axis of the thermistor 57 extends generally parallel to the direction of any fluid flowing along the longitudinal axis of the catheter 11.

The peripheral wall 59 has an outer peripheral surface 69, and the outline of that surface over the opening 61 is a body line 71 of the tube 13. The thermistor 57 extends radially outwardly no farther than about the body line 71 and, in the embodiment illustrated, lies slightly radially inwardly of the body line. The cavity 67 lies radially inwardly of the body line 71, and the thermistor 57 does not extend out of the cavity 67.

A positioning rod 73 and a plug 75 are provided in the thermistor lumen 30 on opposite sides of the mounting body 63. The rod 73 positions the conductors 49 during manufacture, and the plug 75 completely blocks the lumen 30 distally of the opening 61. The rod 73 and the plug 75 have confronting end faces 77 which lie in axially spaced, radial planes.

The mounting body 63 can be constructed in different ways, but preferably, it includes a base 81 of electrical insulating material located between a wall 82 which separates the lumens 25 and 30 and the thermistor 57 and a thermally conductive layer 83. The thermally conductive layer 83 comprises a matrix of electrically insulating material and a filler carried by the matrix. Both the base 81 and the matrix are preferably constructed of a material which is adherent to the tube 13 and which is an electrical insulator. The material of the base 81 is also preferably a good thermal insulator to insulate the thermistor 57 from any fluid flowing in the through lumen 23. Generally, polymeric materials can be used for the base and the matrix with urethane and epoxy being preferred.

The filler is constructed of a material which is more thermally conductive than the electrical insulating material. For example, the filler may be ceramic, carbon, graphite, or a metal, such as silver, nickel, gold, platinum and aluminum. Examples of suitable ceramics are aluminum oxide, aluminum nitride, boron oxide, boron nitride, silicon oxide and silicon nitride. For example, the filler may be in the form of strands, chopped fibers or particles, with dendritic-shaped particles being preferred for improved thermal conductivity.

By way of example, a preferred ceramic-filled epoxy is EP21TDCLV-2AN obtainable from Master Bond Inc. Ceramic is the preferred material for the filler because it is not electrically conductive. If an electrical conductor is used for the filler, care should be taken to assure that the thermistor is properly electrically insulated.

The positioning of the base 81 and the layer 83 can be varied; however, preferably, the base 81 is contiguous the wall 82 and extends from the face 77 of the plug 75 over some or all of the rod 73 and of the conductors 49 on the rod. This seals the lumen 30 proximally of the opening 61 and firmly mounts the rod 73 and the conductors 49 so they are retained against movement in the thermistor lumen 30. The base 81 also seals any space between the plug 75 and the surface of the lumen 30 and adheres the plug 75 within the thermistor lumen 30.

The base 81 may be of various different configurations and, in this embodiment, has a concave outer surface 84 facing outwardly toward the opening 61. Preferably, the outer surface 84 is spaced from the thermistor 57 to provide space between the base 81 and the thermistor for the thermally conductive layer 83. The thermally conductive layer 83 preferably is sandwiched between the thermistor 57 and the base 81 and extends part way around the sides of the thermistor. Thus, the thermally conductive layer is located to facilitate heat transfer from the fluid outside the tube 13 to the thermistor 57. The thermally conductive layer 83 has sufficient electrical insulating or dielectric properties so as to be safely usable.

If desired, a very thin layer 86 of the base material, such as urethane or epoxy, may be placed over the exposed regions of the layer 58 of the thermistor 57 for electrical insulation purposes. The layer 86 is really not part of the mounting body in the sense that it serves any mounting function although it is adhered to the thermistor and the thermally conductive layer 83. The layer 86 is very thin because it is only used for electrical isolation, and it may or may not be considered part of the mounting body 63.

The mounting body 63 can be constructed as shown by way of example in FIGS. 6 and 7. With the rod 73 and plug 75 in place within the thermistor lumen 30, the thermistor 57 is positioned adjacent the opening 61, and the conductors 49 are positioned on the rod 73 as shown in FIG. 6. Although the conductors 49 could extend linearly along the rod 73 if desired, in this embodiment they form two reverse bends 88 and 90 to better retain them between the rod 73 and the wall of the lumen 30. The bends 88 and 90 do not control the height of the thermistor 57 and are spaced well proximally of the bond location 52 where bonding of the segments of the conductors 49 occurs.

With the thermistor 57 supported in the position of FIG. 6, the base 81 is poured through the opening 61 as shown in FIG. 7. After the base 81 has cured, the thermally conductive layer 83 is poured through the opening 61 and allowed to cure to form the structure shown in FIG. 8.

As shown in FIG. 8, the conductors 49 are essentially straight between a location within the passage 79, i.e., the bend 90, and the bond location 52 and preferably all the way to the thermistor 57, or more specifically, to the glass bead 56 thereof. There is no kink or permanent bend in the conductors 49 in this region, and the conductors are not in any way permanently deformed. The slight draping of the conductors 49 shown by way of example in FIGS. 6 and 8 may be the result of the inherent flexibility of these conductors.

If desired, the thermally conductive layer 83 can be omitted, and the entire mounting body can be comprised of the base 81. In this event, the conductive layer 83 is replaced with the base 81 so that the mounting body 63 has the same configuration as the combined base 81 and conductive layer 83 shown in FIG. 8.

Another alternative construction is shown in FIG. 9 which shows a catheter 11a. Portions of the catheter 11a corresponding to portions of the catheter 11 are designated by corresponding reference numerals followed by the letter "a."

The catheter 11a is identical to the catheter 11, except for the mounting body 63a. The mounting body 63a includes a ramp 85 integral with a rod 73a which forms a plug having a central passage 97. The ramp 85 has a ramp surface 87 which is flat and inclined upwardly as it extends proximally. Accordingly, the height or the orientation of the thermistor 57a relative to the body line 71a can be adjusted by moving the ramp 85 longitudinally during assembly. The thermistor 57a may be raised above the ramp as desired for depositing of the mounting body 63a which adheres the thermistor 57a to the ramp 85. The rod 73a and its ramp 85 may be constructed of any material suitable for the base 81 as described above, including polyvinylchloride, as well as a ceramic. The mounting body 63a also includes a thermally conductive layer 83;

The thermistor 57a projects into the cavity 67a below the body line 71a much the same as in FIG. 8. However, the thermistor 57a has its long axis tilted slightly upwardly. In any event, the conductors 49a extend in essentially straight-line fashion through the linear passage 97 to the bond location 52 and to the thermistor 57a with only a large radius curve near the thermistor 57a.

In use of the catheter 11, the catheter tube 13 is introduced through a vein or artery of a patient and into the heart (FIG. 1) using known techniques. The balloon is inflated through the balloon inflation lumen 21, and the inflated balloon is used to carry the distal end 17 of the catheter to the desired location. In the example shown in FIG. 1, the balloon 19 is carried into the pulmonary artery 91. The location of the tube 13 within the heart will depend upon the procedure to be carried out.

For example, to calculate ejection fraction, the tube 13 is inserted into the heart so as to place the injectate port 45 in the right atrium 93, the thermistor 57 into the pulmonary artery 91 and the distal end 17 into the pulmonary artery 91 as shown in FIG. 1. A bolus of cold fluid is then injected into the right atrium 93 through the injectate port 45 and allowed to mix with the bloodstream in the right ventricle 95. The blood and cold fluid mixture flow along the catheter tube and over the thermistor 57 in the pulmonary artery 91. The temperature of the mixture changes with each heatbeat, and the thermistor 57 can track each temperature change so as to provide a stepped temperature chart. This information can then be processed in accordance with known techniques to provide ejection fraction. Pressure can be monitored, if desired, through the through lumen 23.

As shown in FIG. 2, the central lumen 25 and the lumens 27 and 29 are between the thermistor lumen 30 and the through lumen 23 so that the central lumen and the lumens 27 and 29 thermally insulate the thermistor 57 from any fluid carried by the through lumen 23. In this regard, the through lumen 23 may carry a fluid, such as medication, which may be at a temperature different from the temperature being measured by the thermistor. Thus, the lumens 27 and 29 serve as separating lumens to separate the thermistor lumen 30 at least in the radial zone of the tube 13 occupied by the thermistor 57 from the through lumen 23. For example, this radial zone should include the plane of FIG. 2 and have sufficient axial length to properly insulate the thermistor. In the illustrated embodiments, this radial zone may be considered as extending from the plug 47 just distally of the injectate port 45 to the distal end 17 of the tube 13. The balloon inflation lumen also serves this separating and thermal-insulating function.

Although the injectate lumen 27 carries the cold fluid, the cold fluid is discharged at the injectate port 45 which is located proximally of the thermistor 57, and the injectate lumen 27 is plugged distally of the injectate port. Consequently, in the radial zone of the tube 13 occupied by the thermistor 57, the injectate lumen 27 is incapable of conducting fluid through the catheter. Moreover, the injectate lumen 27 and the electrical wires lumen 29 are also plugged at their distal ends and are, therefore, incapable of conducting fluid completely through the catheter and to the radial zone of the tube 13 occupied by the thermistor 57.

Although exemplary embodiments of the invention have been shown and described, many changes, modifications and substitutions may be made by one having ordinary skill in the art without necessarily departing from the spirit and scope of this invention.

We claim:

1. A catheter for temperature measurement of a fluid within a living body, said catheter comprising:
   an elongated tube having an interior and an exterior, sized to be received within a vein or an artery and having proximal and distal ends, a peripheral wall, at least one lumen extending longitudinally within said tube and an opening in said peripheral wall which extends form said lumen to the exterior of said tube;
   a thermistor;
   a thermistor mounting body in said lumen adjacent said opening at least partially defining a cavity at said opening, said cavity opening radially outwardly;
   wherein said mounting body includes a matrix of electrical insulating material and a filler carried by the matrix, said filler being of a material which is more thermally conductive than said electrical insulating material;
   said thermistor being at least partially within said mounting body, with a portion of said thermistor projecting into said cavity whereby said thermistor portion is adapted to be in good heat transfer relationship to the fluid within the body;
   at least one conductor in said tube, at least a region of said conductor being in said lumen and extending along said lumen to said thermistor, said region of the conductor being electrically coupled to said thermistor; and
   said region of said conductor extending generally longitudinally of the lumen from said thermistor to a location proximal to said thermistor, wherein said region of said conductor between said proximal location and said thermistor is essentially coaxial with said lumen.

2. A catheter as defined in claim 1 wherein said region of said conductor between said proximal location and said thermistor is not permanently deformed.

3. A catheter as defined in claim 1 wherein said tube has a body line, said cavity is radially inwardly of said body line and said thermistor lies no farther radially outward than said body line.

4. A catheter as defined in claim 1 wherein said filler is a ceramic.

5. A catheter as defined in claim 1 wherein said mounting body includes an insert received in said lumen and having a ramp on which said thermistor is seated and means for retaining said thermistor on said ramp.

6. A catheter as defined in claim 5 wherein said retaining means and ramp include a polymeric material.

7. A catheter as defined in claim 1 wherein there are a plurality of said lumens, a second of said lumens being a through lumen which opens at a distal port at said distal end of said tube, a third of said lumens being a central lumen and fourth and fifth of said lumens being separating lumens, said central and separating lumens being closed at said distal end and incapable of conducting fluid carried by said through lumen completely through the catheter and to a radial zone of said tube occupied by said thermistor, and said central and separately lumens being between said thermistor lumen and said through lumen whereby the central and separating lumens can thermally insulate said thermistor from any fluid carried by said through lumen.

8. A catheter as defined in claim 11 wherein said filler includes dendritic-shaped ceramic particles.

9. A catheter for measuring the temperature of a fluid with an living body, said catheter comprising:
- an elongated tube having an interior and an exterior, sized to be received within a vein or an artery and having proximal and distal ends, a peripheral wall, at least one lumen extending longitudinally within the tube and an opening in the peripheral wall which extends from the lumen to the exterior of the tube;
- a thermistor;
- a thermistor mounting body in said lumen adjacent said opening at least partially defining a cavity at said opening, said cavity opening radially outwardly;
- wherein said mounting body includes a matrix of electrical insulating material and a filler carried by the matrix, said filler being of a material which is more thermally conductive than said electrical insulating material;
- said thermistor being at least partially within said mounting body and having a portion projecting into said cavity whereby the portion of said thermistor which projects into said cavity is adapted to be in good heat transfer relationship to the fluid within the body;
- at least one conductor in said tube, at least a region of said conductor being in said lumen and extending along said lumen to said thermistor, said region of said conductor being electrically coupled to said thermistor; and
- said region of the conductor being devoid of a sharp permanent bend.

10. A catheter as defined in claim 9 including a thin layer of insulating material over said thermistor.

11. A catheter for measuring the temperature of a fluid within a living body, said catheter comprising:
- an elongated tube having an interior and an exterior, sized to be received within a vein or an artery and having proximal and distal ends, a peripheral wall, at least one lumen extending longitudinally within the tube and an opening in said peripheral wall which extends from said lumen to the exterior of said tube;
- a thermistor;
- a thermistor mounting body in said lumen adjacent said opening;
- said thermistor being at least partially within said mounting body and mounted on said tube by said mounting body; and
- said mounting body including a matrix of electrical insulating material and a filler carried by said matrix, said filler being of a material which is more thermally conductive than said electrical insulating material.

12. A catheter as defined in claim 11 wherein said filler includes a ceramic.

13. A catheter as defined in claim 11 wherein said filler includes carbon.

14. A catheter as defined in claim 11 wherein said filler includes a metal.

15. A catheter as defined in claim 11 wherein said tube includes a wall defining said lumen, said mounting body includes a base of electrical insulating material between said wall and said thermistor and said matrix contacts said thermistor and is adjacent said base.

16. A catheter as defined in claim 15 wherein said electrical insulating material of said base and matrix is selected from the group consisting of urethane and epoxy and said filler is a ceramic.

17. A catheter as defined in claim 11 including a thin layer of electrical insulating material over said thermistor to provide electrical insulation between said thermistor and the fluid within the living body.

18. A catheter as defined in claim 11 wherein said mounting body includes an insert received in said lumen and having a ramp on which said thermistor is seated and means for retaining said thermistor on said ramp.

19. A catheter as defined in claim 18 wherein said retaining means includes said matrix and said filler.

20. A catheter as defined in claim 11 wherein there are a plurality of said lumens, a second of said lumens being a through lumen which opens at a distal port at said distal end of said tube, a third of said lumens being a central lumen and fourth and fifth of said lumens being separating lumens, said central and separating lumens being closed at said distal end and incapable of conducting fluid carried by said through lumen completely through the catheter and to a radial zone of said tube occupied by said thermistor, and said central and separating lumens being between said thermistor lumen and said through lumen whereby the central and separating lumens can thermally insulate said thermistor from any fluid carried by said through lumen.

21. A catheter as defined in claim 11 wherein said mounting body at least partially defines a radially outwardly opening cavity at said opening, said thermistor is partially in said mounting body and projects into said cavity whereby a portion of said thermistor which projects into said cavity is adapted to be in good heat transfer relationship to the fluid within the living body.

22. A catheter for measuring the temperature of a fluid within a living body, said catheter comprising:
- an elongated tube having an interior and an exterior, sized to be received within a vein or an artery and having proximal and distal ends, a peripheral wall, at least one lumen extending longitudinally within said tube and an opening in said peripheral wall which extends from said lumen to said exterior of said tube;
- a thermistor;
- a thermistor mounting body in said lumen adjacent said opening that mounts said thermistor on said tube;
- wherein said mounting body includes a matrix of electrical insulating material and a filler carried by the matrix, said filler being of a material which is more thermally conductive than said electrical insulating material;
- a thermistor being at least partially within said mounting body; and
- said mounting body including an insert received in said lumen and having a ramp for supporting said thermistor and means for retaining said thermistor on said ramp.

23. A catheter as defined in claim 24 wherein said retaining means and ramp include a polymeric material.

24. A catheter as defined in claim 24 wherein said mounting body at least partially defines a radially outwardly opening cavity at said opening, said thermistor is partially in said mounting body and projects into said cavity whereby a portion of said thermistor which projects into said cavity is adapted to be in good heat transfer relationship to the fluid within the living body.

25. A catheter for measuring the temperature of a fluid within a living body, said catheter comprising:
   an elongated tube having an interior and exterior, sized to be received within a vein or an artery and having proximal and distal ends, a peripheral wall and a plurality of lumens extending longitudinally within the tube;
   one of said lumens being a thermistor lumen, said peripheral wall having an opening which extends from said thermistor lumen to said exterior of said tube;
   a thermistor mounted in said thermistor lumen;
   a second of said lumens being a through lumen which opens at a distal port at said distal end of said tube;
   a third of said lumens being a central lumen and fourth and fifth of said lumens being separating lumens, said central and separating lumens being closed at said distal end and incapable of conducting a fluid carried by said through lumen completely through the catheter and to a radial zone of said tube occupied by said thermistor; and
   said central and separating lumen being between said thermistor lumen and said through lumen whereby said central and separating lumens can thermally insulate said thermistor from any fluid carried by said through lumen.

26. A catheter as defined in claim 25 including at least one optical fiber mounted in and filling said central lumen.

27. A catheter as defined in claim 25 wherein said mounting body at least partially defines a radially outwardly opening cavity at said opening, said thermistor is partially in said mounting body and projects into said cavity whereby a portion of said thermistor which projects into said cavity is adapted to be in good heat transfer relationship to the fluid within the body.

28. A method of using the catheter of claim 25 comprising a series of steps including the step of introducing a fluid to said through lumen, at said proximal end, and allowing it to flow to said radial zone and the step of thermally insulating said thermistor from said fluid with said central and separating lumens.

* * * * *